US005849323A

United States Patent [19]
Braswell et al.

[11] Patent Number: 5,849,323
[45] Date of Patent: Dec. 15, 1998

[54] COLLAGEN MIMETIC AND METHOD OF TREATING RHEUMATOID ARTHRITIS USING SAME

[75] Inventors: A. Glenn Braswell, 6100 Lake Forest Dr., NE., Suite 400, Atlanta, Ga. 30328; Aftab J. Ahmed, Marina Del Ray, Calif.

[73] Assignee: A. Glenn Braswell, Atlanta, Ga.

[21] Appl. No.: 873,918

[22] Filed: Jun. 12, 1997

[51] Int. Cl.$^6$ .............. A61K 9/14; A61K 9/20; A61K 38/08; A61K 35/32
[52] U.S. Cl. .......... 424/439; 424/464; 424/489; 424/548; 514/15; 514/825
[58] Field of Search .................. 424/439, 489, 424/464, 548; 514/15, 825

[56] References Cited

U.S. PATENT DOCUMENTS

| | | | |
|---|---|---|---|
| 5,399,347 | 3/1995 | Trentham et al. | 424/184.1 |
| 5,529,786 | 6/1996 | Moore | 424/464 |

OTHER PUBLICATIONS

John Humphries et al., *Current Opinion in Biotechnology*, vol. 2, pp. 539–543, (1991) "Chemical Methods Of Protein Synthesis And Modification".

Prockop et al., "Heritable Disorders of Connective Tissue," Edocrinology and Metabolism, Part 13, Chapter 351, pp. 2105–2117, 1993.

Kakimoto et al., "The Effect of Anti–adhesion Molecule Antibody on the Development of Collagen–Induced Arthritis", Cellular Immunology 142, pp. 326–337 (1992).

Bakker et al., "Experimental Immune Mediated Arthritis in Rhesus Monkeys: A Model for Human Rhesus Monkeys", Rheumatology International, pp. 21–29 (1990).

Ahmed, "Immune Cocktail, Anyone", Journal of Longevity Reseach, vol. 1/No. 7, pp. 6–7 (1995).

Sieper et al., "Oral Type II Collagen Treatment in Early Eheumatoid Arthritis", Arthritis & Rheumatism, vol. 39, No. 1, pp. 41–51 (Jan. 1996).

Trentham et al., "Effects of Oral Adminstration of Type II Collagen on Rheumatoid Arthritis", Science, vol. 261, (24 Sep. 1993).

Alberts et al., "Cell Junctions, Cell Adhesion, and the Extracelluar Matrix", Biology of the Cell, vol. 1, Chapter 19, pp. 978–986 (1994).

*Primary Examiner*—Thurman K. Page
*Assistant Examiner*—James M. Spear
*Attorney, Agent, or Firm*—Oliff & Berridge, PLC

[57] ABSTRACT

A collagen mimetic peptide having the nine amino acid sequence glycine-proline-hydroxyproline-glycine -proline-glutamine-glycine-methionine-glycine, and analogs thereof is described. The collagen mimetic peptide may be included within a pharmaceutical composition also containing a pharmaceutically acceptable carrier and/or animal tissue. The collagen mimetic peptide is used in a treatment of rheumatoid arthritis by orally administering the collagen mimetic in an amount effective to reduce or alleviate one or more symptoms associated with rheumatoid arthritis.

19 Claims, No Drawings

COLLAGEN MIMETIC AND METHOD OF TREATING RHEUMATOID ARTHRITIS USING SAME

BACKGROUND OF THE INVENTION

1. Field of the Invention

This invention relates to a specific collagen mimetic peptide, pharmaceutical compositions containing the peptide, and a method of treating rheumatoid arthritis through the oral administration of the peptide and/or pharmaceutical composition.

2. Discussion of Related Art

Rheumatoid arthritis is an autoimmune disease wherein the immune system of the body mistakenly perceives the body's own collagen as foreign and mounts an abnormal immune response against it. Rheumatoid arthritis is characterized by persistent swollen and inflamed joints, and progresses into the destruction of cartilage and the erosion of bone, ultimately leading to destruction of joints. Collagen, in particular Type II collagen, is a major component of cartilage that is particularly affected.

Known treatments for arthritis have involved the use of nonspecific immunosuppressive drugs which suppress the entire immune system and are incapable of selectively suppressing the abnormal autoimmune response. This restraint of the immune system also increases the risk of infection. In addition, prolonged use of such drugs can entail severe toxic side effects. Moreover, such immunosuppressive drugs are only partially effective in mitigating symptoms of rheumatoid arthritis, and this partial effectiveness greatly decreases even more over time.

Other known treatments for rheumatoid arthritis include the use of steroids and nonsteroidal anti-inflammatory agents. However, these agents can also result in significant toxicity and are again only partially effective in mitigating symptoms of rheumatoid arthritis.

Collagen directly injected into affected joints is also ineffective because the immune system of the body attacks and destroys the injected collagen similar to the body's own collagen.

Due to the phenomenon of oral tolerance, treatments of autoimmune diseases such as rheumatoid arthritis through the oral ingestion of proteins such as collagen are becoming increasingly popular. Oral tolerization involves ingestion, like food, of the antigen attributed to trigger the autoimmunity. When such an exogenous protein enters the body via the digestive tract, it circumvents the body's immune surveillance. Studies have employed oral tolerization in animals to suppress autoimmune diseases including multiple sclerosis, diabetes and rheumatoid arthritis.

Treatments of rheumatoid arthritis utilizing oral tolerization are known. For example, U.S. Pat. No. 5,529,786 treats rheumatoid arthritis in humans with a pill that includes whole Type II collagen. U.S. Pat. No. 5,399,347 employs the administration of whole collagen or long amino acid sequence biologically active peptide fragments of whole collagen. These patents are expressly incorporated herein by reference in their entireties. Neither reference discloses or suggests a collagen mimetic peptide having a specific nine amino acid sequence.

SUMMARY OF THE INVENTION

It is one object of the present invention to develop a peptide that when orally ingested into the body of a mammal forms Type II collagen in vivo. It is a further object to develop a pharmaceutical composition containing the peptide.

A still further object of the present invention is to develop a treatment method of rheumatoid arthritis in which through oral ingestion of the peptide of the invention, one or more symptoms associated with rheumatoid arthritis are reduced or alleviated.

These and other objects of the invention are achieved from a collagen mimetic peptide containing nine amino acids, and analogs thereof. The peptide and analogs thereof are preferably included within a pharmaceutical composition suitable for oral administration to a mammal.

The objects of the invention are further achieved by a method of treating rheumatoid arthritis in which the peptide is orally administered to a mammal suffering from symptoms associated with rheumatoid arthritis in an amount effective to reduce or alleviate one or more such symptoms. Typically symptoms of rheumatoid arthritis include inflammation of synovial membranes, joint swelling, inflammation, stiffness and pain.

DETAILED DESCRIPTION OF PREFERRED EMBODIMENTS

The collagen mimetic of the present invention comprises a peptide of nine amino acids having the sequence:

glycine-proline-hydroxyproline-glycine-proline-glutamine-glycine-methionine-glycine.

The amino acids in the collagen mimetic are all represented in naturally occurring Type II collagen.

In addition to the above peptide sequence, the collagen mimetic of the invention also includes close structural analogs of the nine amino acid sequence. By "analogs" is meant a peptide of nine amino acids structurally similar to the nine amino acid sequence set forth above but in which one or more of the amino acids other than glycine are substituted with other amino acids while retaining substantially the same ability to form Type II collagen in vivo. The glycine must remain invariant in the peptide sequence because glycine is the only amino acid small enough to facilitate three-dimensional formation and viability of the collagen protein triple helix.

The collagen mimetic peptide according to the invention may be synthesized in accordance with any method known in the art. A preferred method for peptide synthesis is the liquid-phase method. In this method, amino acids are linked to a carboxyl group that has been activated by reacting with a reagent such as, for example, dicyclohexylcarbodiimide (DCC). The reaction of a free amino acid on the activated carboxyl group leads to the formation of a peptide bond and the release of dicyclohexylurea. In order to link the amino acids together, it is necessary that only a single amino group and a single carboxyl group be available for reaction. Thus, it is necessary to block (protect) all other potentially reactive groups during the synthesis. This sequential protection and de-protection is carried out at each successive step of the peptide synthesis.

A review on peptide synthesis generally can be found in Bodansky et al., "The Practice of Peptide Synthesis," Springer-Verlag, Berlin, 1984 and Humphries et al., Curr. Opinion Biotech., volume 2, page 539 (1991). The discussion in these references is herein incorporated by reference in its entirety.

The collagen mimetic peptide may be added to foods and/or liquids for ingestion by a mammal. By "mammal" is meant any organism having an immune system and that is susceptible to an autoimmune diseases. "Mammal" is understood to include humans. The foods and/or liquids to which the collagen mimetic peptide is added are preferably slightly acidic, for example, nutritious fluids such as orange juice.

The collagen mimetic is most preferably incorporated into a pharmaceutical composition suitable for oral ingestion by a mammal. The pharmaceutical composition may take the form of a solid or liquid. The pharmaceutical composition preferably also includes a pharmaceutically acceptable carrier.

For solid form preparations such as, for example, powders, tablets, granules, capsules and the like, the solid carrier may be one or more substances such as diluents, fillers, flavoring agents, solubilizers, lubricants, suspending agents, binders, tablet disintegrating agents, encapsulating materials and the like. Specific suitable carrier materials include, for example, magnesium carbonate, calcium carbonate, sodium bicarbonate, magnesium stearate, calcium stearate, talc, lactose, sugar, pectin, gelatin, dextrin, starch, tragacanth, cellulose derivatives, methyl cellulose, sodium carboxymethyl cellulose, low melting waxes, cocoa butter, alginates, polyvinyl pyrrolidone, polyethyl glycols, quaternary ammonium compounds and the like.

The solid form preparations may also take the form of sustained release systems. Sustained release delivery vehicles, such as capsules, are well known in the art.

Liquid form preparations may include, for example, solutions, suspensions and emulsions. Specific suitable carriers for liquid form preparations include, for example, water, coloring agents, flavoring agents, emulsifing agents, stabilizers and thickening agents. Additional specific examples include, for example, syrup and dextrose. Viscous materials such as natural synthetic gums, resins, methyl cellulose, sodium carboxy cellulose and other agents known to the pharmaceutical art may also be used.

Any suitable method for preparing the solid or liquid preparations mentioned above, which methods are known in the art, may be used. The particular method used will depend upon the form of the composition being prepared as readily understood by one of ordinary skill in the art.

A single dose unit of the peptide and/or pharmaceutical composition may contain, for example, 0.01 to 10 mg, preferably 0.05 to 5 mg, more preferably 0.7 to 1 mg of the collagen mimetic peptide.

The collage mimetic is preferably administered in single dosage units one to four times daily. In an effort to enhance absorption of the collagen mimetic, the collagen mimetic is most preferably administered on an empty stomach, for example at least one-half hour before eating, and most preferably two hours or more after eating and before eating again.

The collagen mimetic should be orally administered in an amount effective to reduce one or more symptoms such as swelling, inflammation, pain, stiffness and the like associated with rheumatoid arthritis. The collagen mimetic is preferably administered in single dose amounts of, for example, 0.1 to 100 µg, preferably 1 to 15 µg, most preferably 10 µg per kg of body weight. The total daily amount of collagen mimetic administered to an average size adult human is, for example, 0.01 to 10 mg, * preferably 0.05 to 5 mg, more preferably 0.1 to 1 mg total. As mentioned above, the total daily amount administered may be achieved in a single dose or over the course of several doses spaced throughout the daily eating cycle of the mammal.

In a most preferred embodiment, the collagen mimetic is included in a pharmaceutical composition in conjunction with animal tissue. The animal tissue is preferably cartilage, a potential source of whole collagen, in particular whole Type II collagen.

The animal tissue may most preferably comprise, for example, bovine cartilage homogenate. Bovine cartilage homogenate contains not only whole Type II collagen, but also about 30% by weight proteoglycans. Proteoglycans are structural components of cartilage in the body. The addition of bovine cartilage homogenate and other similar animal tissues thus provides the additional benefit of adding additional structural integrity to body parts (i.e., joints) affected by rheumatoid arthritis.

Bovine cartilage homogenate may be obtained in any suitable manner such as, for example grinding, pulverizing and/or comminuting bovine cartilage. In a preferred method, the bovine cartilage homogenate, or similar animal tissue, is derived from pulverization of deep-frozen tissue in a phosphate buffer at physiological pH in a homogenizer, sonicator or the like. The obtained gemisch is centrifuged at low speed to remove any debris. The supernatant is retrieved and freeze-dried for inclusion in the formulation. The animal tissue may preferably form the balance of the dosage form, which also includes the collagen mimetic, fillers, excipients and the like.

Without being bound by theory, it is believed that once the collagen mimetic is ingested by a mammal, the collagen mimetic will be taken into the mammalian system through the digestive tract. Due to oral tolerance, the collage mimetic is not attacked by the immune system of the mammal.

It is believed that the peptide having the nine amino acid sequence is first put together into amino acid strands of 18 amino acids, which are then formed into the 54 nucleotide triple helix of the collagen protein. In other words, the collagen mimetic induces the formation of collagen in vivo, which collagen formation occurs free of attack from the immune system due to the collagen mimetic having been orally introduced into the mammalian system.

The formation of collagen in vivo is well understood in the art. See, for example, Prockop et al., "Heritable Disorders of Connective Tissue," Endocrinology and Metabolism, Part 13, Chapter 351, pages 2105–2117.

The invention is further described by way of the following example.

Four human patients, each suffering from rheumatoid arthritis, were selected for a study of the effectiveness of a dietary supplement comprising Type II collagen mimetic having a nine amino acid sequence of glycine-proline-hydroxyproline-glycine-proline glutamine -glycine-methionine-glycine in combination with bovine cartilage homogenate. Half of the patients were given the dietary supplement while the other half received a placebo.

The patients are each administered the composition twice daily on an empty stomach, i.e., roughly two to three hours prior to the intake of any food. Each of the patients is asked to record their perceived sense of well-being, in particular the degree of pain in various joints throughout the body including shoulder, elbow, wrist, finger, hip, knee, ankle and toe. The study lasts seven weeks.

All of the patients receiving the collagen mimetic reported palpable mitigation of symptoms associated with rheumatoid arthritis within three weeks of the start of the regimen. The patients' subjective assessment is evaluated and verified by a clinical investigator through bi-weekly visits. The symptoms did not plateau off during the seven weeks of the study.

During the course of the study, a midstream quasi-cross over is instituted. Subjects who had been receiving the collagen mimetic are reverted to placebo. Following reversion to the placebo, these patients did not report any recurrence of symptoms for about three weeks following reversion. Patients originally on the placebo who are switched to the collagen mimetic reported alleviation of symptoms within three weeks of their reversion.

None of the patients in the study reported any adverse reactions or other side-effects from the taking of the collagen mimetic.

What is claimed is:

1. A collagen mimetic peptide consisting of the nine amino acid sequence glycine-proline-hydroxyproline-glycine-proline-glutamine-glycine-methionine-glycine or analogs thereof.

2. A composition, the composition comprising a collagen mimetic peptide having the nine amino acid sequence glycine-proline-hydroxyproline-glycine-proline-glutamine-glycine-methionine-glycine or analogs thereof, wherein the composition contains from 0.01 to 10 mg of the collagen mimetic peptide.

3. A composition according to claim 2, wherein the composition further comprises a pharmaceutically acceptable carrier.

4. A composition according to claim 2, wherein the composition further comprises animal tissue.

5. A composition according to claim 4, wherein the animal tissue is bovine cartilage homogenate.

6. A composition according to claim 2, wherein the composition contains from 0.05 to 5 mg of the collagen mimetic peptide.

7. A composition according to claim 2, wherein the composition contains from 0.1 to 1 mg of the collagen mimetic peptide.

8. A composition according to claim 2, wherein the composition is in the form of a solid.

9. A composition according to claim 2, wherein the composition is in the form of a liquid.

10. A method of treating rheumatoid arthritis, the method comprising orally administering a collagen mimetic peptide having the nine amino acid sequence glycine-proline-hydroxyproline-glycine-proline-glutamine-glycine-methionine-glycine or analogs thereof in an amount effective to reduce or alleviate at least one symptom associated with rheumatoid arthritis, wherein the collagen mimetic peptide is administered in a total daily amount of from 0.01 to 10 mg.

11. A method according to claim 10, wherein the collagen mimetic peptide is present in a composition.

12. A method according to claim 11, wherein the composition further contains a pharmaceutically acceptable carrier.

13. A method according to claim 11, wherein the composition further contains animal tissue.

14. A method according to claim 10, wherein the collagen mimetic peptide is orally administered at least two hours before the ingestion of food.

15. A method according to claim 10, wherein a one dosage unit of collagen mimetic peptide contains 0.05 to 10 mg of the collagen mimetic peptide.

16. A method according to claim 10, wherein the collagen mimetic peptide is administered in a total daily amount of from 0.05 to 5 mg.

17. A method according to claim 10, wherein the collagen mimetic peptide is orally administered in single doses one to four times daily.

18. A method according to claim 10, wherein the at least one symptom comprises joint swelling, joint inflammation, stiffness or pain.

19. A method according to claim 10, wherein the collagen mimetic peptide is administered in a total daily amount of from 0.1 to 1 mg.

* * * * *